(12) United States Patent
Goetzinger et al.

(10) Patent No.: US 8,834,752 B2
(45) Date of Patent: Sep. 16, 2014

(54) SYSTEMS AND METHODS FOR MAKING LAYERED DENTAL APPLIANCES

(75) Inventors: Martin Goetzinger, Eching am Ammersee (DE); Holger Hauptmann, Sindelsdorf (DE); Gallus Schechner, Seefeld (DE); Michael Jahns, Gilching (DE)

(73) Assignee: 3M Innovative Properties Company, St. Paul, MN (US)

( * ) Notice: Subject to any disclaimer, the term of this patent is extended or adjusted under 35 U.S.C. 154(b) by 276 days.

(21) Appl. No.: 13/497,410

(22) PCT Filed: Sep. 22, 2010

(86) PCT No.: PCT/US2010/049786
§ 371 (c)(1),
(2), (4) Date: Mar. 21, 2012

(87) PCT Pub. No.: WO2011/041182
PCT Pub. Date: Apr. 7, 2011

(65) Prior Publication Data
US 2012/0175802 A1    Jul. 12, 2012

Related U.S. Application Data

(60) Provisional application No. 61/247,265, filed on Sep. 30, 2009.

(51) Int. Cl.
| | |
|---|---|
| *A61C 13/09* | (2006.01) |
| *B28B 1/16* | (2006.01) |
| *B28B 1/30* | (2006.01) |
| *B28B 7/28* | (2006.01) |
| *A61C 13/00* | (2006.01) |

(52) U.S. Cl.
CPC ............ *A61C 13/0003* (2013.01); *A61C 13/09* (2013.01)

USPC ............ 264/16; 264/669; 264/621; 264/642; 433/167

(58) Field of Classification Search
None
See application file for complete search history.

(56) References Cited

U.S. PATENT DOCUMENTS

| | | | |
|---|---|---|---|
| 3,810,773 | A | 5/1974 | Shannon |
| 4,078,310 | A | 3/1978 | Horger |

(Continued)

FOREIGN PATENT DOCUMENTS

| | | |
|---|---|---|
| DE | 19922870 | 7/2000 |
| EP | 0311214 | 4/1989 |

(Continued)

OTHER PUBLICATIONS

K. Prabhakaran, "Casting of Alumina Using Boehmite as a Binder", Journal Eur. Ceram. Soc., 19 (1999) 2875-2881.

(Continued)

*Primary Examiner* — Benjamin Schiffman
(74) *Attorney, Agent, or Firm* — Nicole J. Einerson

(57) ABSTRACT

A system and method for making a layered dental appliance. The system can include a first mold comprising a negative of a first layer of a layered dental appliance, a second mold comprising a negative of a second layer, and a dental core dimensioned to be at least partially received in the first mold and the second mold. The method can include positioning a first slurry in the first mold, and pressing the dental core into the first slurry to form a first article comprising the dental core and a first layer formed from the first slurry. The method can further include removing the first article from the first mold, positioning a second slurry in the second mold, and pressing the first article into the second slurry to form a second article comprising the dental core, the first layer, and a second layer formed from the second slurry.

11 Claims, 2 Drawing Sheets

(56) References Cited

U.S. PATENT DOCUMENTS

| | | |
|---|---|---|
| 4,115,487 A | 9/1978 | Rockett |
| 4,321,042 A | 3/1982 | Scheicher |
| 4,937,928 A | 7/1990 | Van der Zel |
| 5,028,362 A | 7/1991 | Janney |
| 5,204,055 A | 4/1993 | Sachs |
| 5,342,201 A | 8/1994 | Oden |
| 5,697,043 A | 12/1997 | Baskaran |
| 5,989,031 A | 11/1999 | Kura |
| 6,395,202 B1 | 5/2002 | Nagel |
| 6,648,645 B1 | 11/2003 | MacDougald |
| 6,869,552 B2 | 3/2005 | Glidewell |
| 6,955,776 B1 | 10/2005 | Feenstra |
| 7,086,863 B2 | 8/2006 | Van der Zel |
| 7,181,862 B2 | 2/2007 | Boara |
| 7,236,842 B2 | 6/2007 | Kopelman |
| 7,384,470 B2 | 6/2008 | Binkle |
| 7,446,057 B2 | 11/2008 | Bietsch |
| 7,536,234 B2 | 5/2009 | Kopelman |
| 7,689,310 B2 | 3/2010 | Kopelman |
| 2002/0157419 A1 | 10/2002 | Ganguli |
| 2003/0222366 A1 | 12/2003 | Stangel |
| 2005/0023710 A1 | 2/2005 | Brodkin |
| 2006/0008777 A1 | 1/2006 | Peterson |
| 2006/0151911 A1 | 7/2006 | Zollner |
| 2006/0257824 A1 | 11/2006 | Pfeiffer |
| 2007/0092853 A1 | 4/2007 | Liu |
| 2008/0131841 A1 | 6/2008 | Taub |
| 2008/0206460 A1 | 8/2008 | Rhoades |
| 2008/0241788 A1 | 10/2008 | Bauer |
| 2008/0302135 A1 | 12/2008 | Costa |
| 2008/0318189 A1 | 12/2008 | Brodkin |
| 2009/0233258 A1 | 9/2009 | Luthardt |
| 2009/0311649 A1 | 12/2009 | Detje |
| 2009/0311650 A1 | 12/2009 | Stephan |
| 2010/0167238 A1 | 7/2010 | Kopelman |
| 2010/0233655 A1 | 9/2010 | Karim |
| 2010/0248189 A1 | 9/2010 | Burger |

FOREIGN PATENT DOCUMENTS

| | | |
|---|---|---|
| EP | 0455854 | 11/1991 |
| EP | 0943296 | 9/1999 |
| EP | 1250895 | 10/2002 |
| EP | 1258456 | 11/2002 |
| EP | 1252867 | 7/2005 |
| EP | 1561433 | 8/2005 |
| EP | 1661866 | 5/2006 |
| EP | 1972321 | 9/2008 |
| EP | 1992302 | 11/2008 |
| GB | 418160 | 10/1934 |
| JP | 01-258920 | 10/1989 |
| JP | 2004-298599 | 10/2004 |
| WO | WO 94/27517 | 12/1994 |
| WO | WO 97/44291 | 11/1997 |
| WO | WO 01/13814 | 3/2001 |
| WO | WO 01/53225 | 7/2001 |
| WO | WO 03/093195 | 11/2003 |
| WO | WO 2004/063105 | 7/2004 |
| WO | WO 2006/120255 | 11/2006 |
| WO | WO 2007/028787 | 3/2007 |
| WO | WO 2007/051447 | 5/2007 |
| WO | WO 2009/070469 | 6/2009 |
| WO | WO 2010/039910 | 4/2010 |
| WO | WO 2010/053698 | 5/2010 |
| WO | WO 2010/074890 | 7/2010 |
| WO | WO 2010/110650 | 9/2010 |
| WO | WO 2010/110662 | 9/2010 |
| WO | WO 2011/041193 | 4/2011 |
| WO | WO 2011/041194 | 4/2011 |
| WO | WO 2011/075349 | 6/2011 |

OTHER PUBLICATIONS

Ullmann's Encyclopedia of Industrial Chemistry (2008), Chapter Silica, Section 4.1 and 5.2.

Ullmann's Encyclopedia of Industrial Chemistry (2005) Chapter Inorganic Polymers, pp. 1-39.

Beuer et al., "High-Strength CAD/CAM-fabricated veneering material sintered to zirconia coping s—A new fabrication mode for all-ceramic restorations"; Dental Materials 25 (2009) 121-128.

International Search Report PCT/US2010/049786; Jan. 14, 2011, 4 pages.

SYSTEMS AND METHODS FOR MAKING LAYERED DENTAL APPLIANCES

CROSS REFERENCE TO RELATED APPLICATIONS

This is a national stage filing under 35 U.S.C. 371 of PCT/US2010/049786, filed 22 Sep. 2010, which claims priority to U.S. Provisional Application No. 61/247,265, filed 30 Sep. 2009, the disclosure of which is incorporated by reference herein in its entirety.

FIELD

The present disclosure is generally directed to systems and methods for making dental appliances, and particularly, to systems and methods for making layered dental appliances.

BACKGROUND

Some existing dental restorations, such as crowns, formed of glass and/or glass ceramic materials are produced by grinding bodies of compacted and heat treated glass and/or glass ceramic particles. Such bodies can be produced by mechanical compacting (e.g. uniaxial pressing) of inorganic powders often together with an organic binder first. The shape of the resulting compacted body can be limited to the shape of the compacting tool used. In some cases, cylindrical or cuboid shaped bodies can be obtained. Such compacted bodies can then undergo a heat treatment to increase the mechanical strength of the compacted bodies. Such a heat treatment can take place at a temperature that causes at least partial sintering of the powder. During such a sintering step, the density of the body of compacted powder can be increased. The resulting compacted and heat treated bodies can then be adhesively fixed in a frame or attached to a holder to prepare them for grinding to a desired shape (e.g. a dental crown or dental facing). The ground bodies can then be removed from the frame. Machining of the compacted bodies which have not been heat treated may not be possible due to the low mechanical strength of the compacted powder.

In addition, in some existing dental systems, a core is milled and then sintered (e.g., to full density). A veneer can also be milled from a mill blank and fused to the core, for example, with a slurry forming an intermediate layer between the core and the veneer. The veneer can then be sintered to the core.

Moreover, in some existing dental systems, dental restorations, such as crowns, can be produced using a manual process of covering a core layer-by-layer with veneering slurries (e.g., using a small brush). Firing steps can be included after application of each layer.

SUMMARY

Some aspects of the present disclosure provide a method for making a layered dental appliance. The method can include providing a dental core, and providing a first mold comprising a negative of a first layer of a layered dental appliance. The method can further include positioning a first slurry in the first mold, and pressing the dental core into the first slurry in the first mold to form a first article comprising the dental core and a first layer formed from the first slurry. The method can further include removing the first article from the first mold. The method can further include providing a second mold comprising a negative of a second layer of a layered dental appliance, and positioning a second slurry in the second mold. The method can further include pressing the first article into the second slurry in the second mold to form a second article comprising the dental core, the first layer, and a second layer formed from the second slurry.

Some aspects of the present disclosure provide a system for making a layered dental appliance. The system can include a first mold comprising a negative of a first layer of a layered dental appliance, and a second mold comprising a negative of a second layer of a layered dental appliance. The system can further include a dental core dimensioned to be at least partially received in the first mold and the second mold. The system can further include a first slurry adapted to be positioned in the first mold to form a first article comprising a first layer on the dental core, wherein the second mold is dimensioned to receive the first article, and a second slurry adapted to be positioned in the second mold to form a second layer on the first article.

Some aspects of the present disclosure provide a method for making a layered dental appliance. The method can include providing a dental core, and providing a mold comprising a negative of an outer shape of a layered dental appliance. The method can further include positioning a first slurry in the mold, and pressing the dental core into the first slurry in the mold to form a first article comprising the dental core and a first layer formed from the first slurry. The method can further include removing the first article from the mold, and firing the first article to shrink at least a portion of the first article and form a fired first article. The method can further include positioning a second slurry in the mold, and pressing the fired first article into the second slurry in the mold to form a second article comprising the dental core, the first layer, and a second layer formed from the second slurry.

Some aspects of the present disclosure provide a system for making a layered dental appliance. The system can include a mold comprising a negative of an outer shape of a layered dental appliance, and a dental core dimensioned to be at least partially received in the mold. The system can further include a first slurry adapted to be positioned in the mold to form a first layer on the dental core, and a second slurry adapted to be positioned in the mold to form a second layer on the dental core.

Other features and aspects of the present disclosure will become apparent by consideration of the detailed description and accompanying drawings.

DETAILED DESCRIPTION

Figure 1:
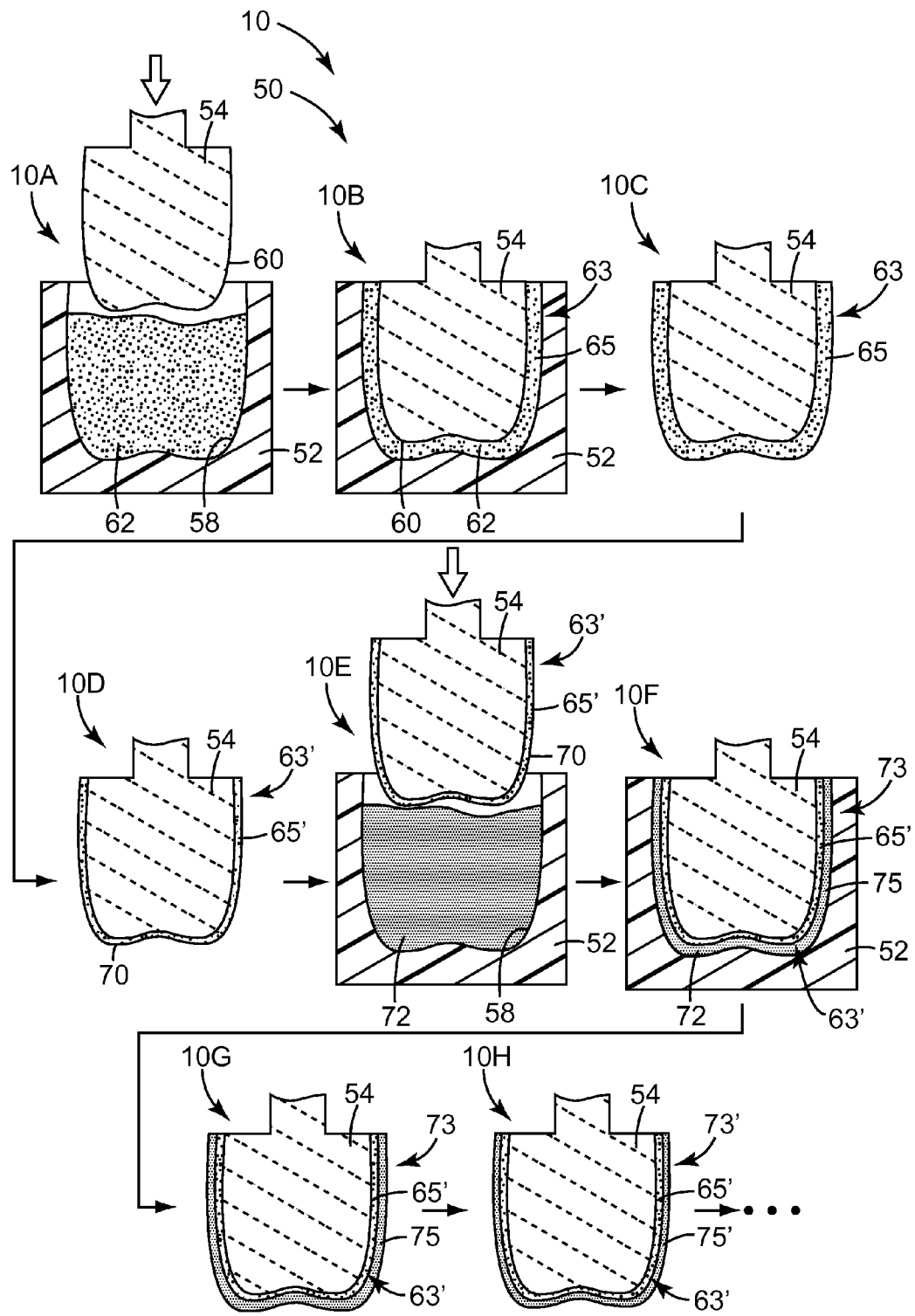
FIG. 1 is a schematic flowchart of a method according to one embodiment of the present disclosure and illustrates a system according to one embodiment of the present disclosure.

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the term "coupled" and variations thereof is used broadly and encompasses both direct and indirect couplings. Further, "coupled" is not restricted to physical or mechanical connections or couplings. It is to be understood that other embodiments may be utilized, and structural or logical changes may be made without departing from the scope of the present disclosure.

The present disclosure generally relates to systems and methods for making layered dental appliances, such as dental restorations. In some embodiments, a dental appliance such as a dental restoration, can be desired that not only meets the performance or material requirements but is also visually indistinguishable from adjacent natural tooth surfaces. A layered dental appliance can have improved aesthetics over a single layer or single material appliance, for example, if one or more layers toward the outer surface of the appliance are more translucent than inner layer(s), such that the appliance (e.g., restoration) more closely mimics the appearance of a natural tooth.

In some embodiments, the systems and methods of the present disclosure may not be performed in situ, or in a patient's mouth. Rather, in some embodiments, the systems and methods of the present disclosure can be employed in a laboratory setting, such as in a dental laboratory. That is, in some embodiments, the methods of the present disclosure can be referred to as lab-bench, desktop, or laboratory procedures.

Some systems and methods of the present disclosure can produce net-shape or near-net-shape dental appliances (e.g., restorations) via a gel casting process (e.g., a solgel casting process), for example, using silica glass as an inorganic binder. Multiple casting steps can be performed consecutively to achieve layered structures.

Some systems and methods of the present disclosure can include providing a first mold that includes a negative of a first layer and a dental core that forms the innermost core of the resulting dental appliance. In such systems and methods, a layered dental appliance can be formed using a gel casting process. In some embodiments, the same mold can be used to form successively outer layers, for example, beginning with a first layer that is formed between the mold and the dental core, a second layer that is formed between the first layer and the mold, and so on. In some embodiments, a second mold that is different than the first mold can be employed for forming the second layer over the first layer. Following the methods of the present disclosure, the innermost layer of the dental appliance would be formed on the dental core first, followed by the next outer layer, followed by the next outer layer, etc., to form as many layers as desired. As a result, the methods of the present disclosure can sometimes be referred to as an "inside-out" method of making a layered dental appliance. Other examples of "inside-out" methods and systems for making a layered dental appliance are described in co-pending U.S. Application No. 61/247,256, filed Sep. 30, 2009, the disclosure of which is incorporated herein by reference.

The term "dental article" is to be understood as an article which can and is to be used in the dental or orthodontic area including dental laboratories.

The term "dental appliance" generally refers to any dental or orthodontic restoration, dental mill blank, prosthetic device, or combination thereof. The appliance may be a finished appliance ready for introduction into the mouth of a patient, an appliance without the finishing (e.g. without stains) but with its final shape (i.e., a "net shape" appliance), or it may be a preformed or near-final dental appliance (i.e., a "near-net shape" appliance) subject to further processing before use, such as a dental mill blank.

The phrase "dental mill blank" generally refers to a solid block of material from which a desired product (e.g., a dental restoration) can be machined. A dental mill blank may have a size of about 10 mm to about 30 mm in two dimensions, for example may have a diameter in that range, and may be of a certain length in a third dimension. A blank for making a single crown may have a length of about 15 mm to about 30 mm, and a blank for making bridges may have a length of about 40 mm to about 80 mm. In some embodiments, a blank used for making a single crown can have a diameter of about 24 mm and a length of about 19 mm. In some embodiments, a blank used for making bridges can have a diameter of about 24 mm and a length of about 58 mm.

The term "machining" generally refers to shaping a material by a machine, and can include, but is not limited to one or more of milling, grinding, cutting, carving, or a combination thereof. In some cases, milling can be faster and more cost-effective than grinding.

The phrase "dental workpiece" generally refers to a dental appliance which has been further processed (e.g. by machining) to obtain an intentionally shaped product. A dental workpiece can be further processed (e.g. by sintering) or used as such.

The phrase "dental restoration" is generally used to refer to any restoration that can be used in the dental field, including, but not limited to, crowns, partial crowns, inlays, onlays, abutments, bridges (e.g., including 2-part, 3-part, 4-part, 5-part or 6-part bridges), implants, other suitable dental articles, and combinations thereof. The dental restoration can include a three-dimensional inner and outer surface including convex and concave structures. Compared to other ceramic articles, such as pottery or paving stones, dental restorations can be relatively small and can include filigree. The thickness of a dental restoration can vary from very thin, for example at its edges and rims (e.g., less than about 0.1 mm) to considerably thick, for example, in the biting, or occlusal, area (e.g., up to about 7 mm). In some embodiments, the thickness of a dental restoration ranges from 0.3 mm to 0.5 mm. In some embodiments, the dental restoration can comprise or consist essentially of a glass; glass ceramic; polycrystalline ceramic material, for example, comprising alumina (e.g., $Al_2O_3$), zirconia ($ZrO_2$), partly or fully stabilized zirconia (e.g., Yttrium-stabilized zirconia), titanium dioxide ($TiO_2$), high-strength oxides of the elements of the main groups II, III and IV and the subgroups III and IV, and their mixtures; metals, metal alloys, precious metals, precious metal alloys, or combinations thereof (e.g., cobalt alloys, such as cobalt-chromium, titanium alloys, gold/platinum/palladium alloys, etc., and combinations thereof); and combinations thereof. In some embodiments, the dental restoration can include at least two layers, for example, a dental core (or dental framework) and a dental veneer.

The phrase "dental core" or "dental framework" generally refers to a solid structure that can be pre-fabricated or at least partially pre-fabricated and then used as the innermost core or center layer of the layered dental appliance of the present disclosure. For example, in some embodiments, the dental core can be adapted to be coupled to or to fit over one or more of a tooth stump, an implant abutment, or the like, or combinations thereof.

The phrase "dental veneer" generally refers to a structure formed of one or more layers that can be coupled (e.g., fused) to or built upon another structure (e.g., a dental core) for color, aesthetics, texture, surface properties, etc., and, in some embodiments, to mimic the appearance of a natural tooth.

A dental core (sometimes referred to as a "dental framework") and a dental veneer can each include a three-dimensional inner and outer surface including convex and concave structures. The outer surface of the dental core can correspond to an inner surface of the dental veneer. The inner surface of the dental core can correspond to an outer surface of a prepared tooth stump, whereas the outer surface of the dental veneer can correspond to the desired (e.g., final) dental restoration.

Dental cores or frameworks can be made of or comprise at least one of a ceramic, a metal, a metal alloy, a precious metal, a precious metal alloy, and combinations thereof. Examples of ceramics can include, but are not limited to, alumina (e.g., $Al_2O_3$); zirconia ($ZrO_2$); partly or fully stabilized zirconia (e.g., Yttrium-stabilized zirconia); titanium dioxide ($TiO_2$); high-strength oxides of the elements of the main groups II, III and IV and the subgroups III and IV, and combinations thereof and combinations thereof. Examples of metals, metal alloys, precious metals, and precious metal alloys can include, but are not limited to, cobalt alloys (e.g., cobalt-chromium), titanium alloys, gold/platinum/palladium alloys, and combinations thereof.

Compared to other framework such as pottery or paving stones, dental cores or framework can be small and filigree, and of high strength. The thickness of the dental framework can vary from very thin, e.g. at the edges and rims (below about 0.1 mm) to considerably thick, e.g. in the biting area (up to about 7 mm).

In some embodiments, the dental core can be pre-sintered or finely sintered prior to be being positioned in the mold to form additional layers on the dental core.

Dental veneers can include one or more layers that would be coupled (e.g., fused) to or built upon an inner core or center of a dental appliance. Dental veneers can also be small and filigree objects. The strength of dental veneers, however, can be less compared to dental frameworks. Dental veneers can be made of or comprise glass and/or glass ceramic materials. Examples of suitable glass materials include, but are not limited to, silica ($SiO_2$) in combination with one or more of alumina ($Al_2O_3$), potassium oxide ($K_2O$), sodium oxide ($Na_2O$), etc., and combinations thereof. Examples of suitable glass ceramic materials include, but are not limited to a material having a glass fraction comprising silica ($SiO_2$) in combination with one or more of alumina ($Al_2O_3$), potassium oxide ($K_2O$), sodium oxide ($Na_2O$), etc., and combinations thereof, and a crystalline fraction comprising e.g. leucite, lithium disilicate, etc., and combinations thereof.

In some embodiments, it can be important to match the coefficient of thermal expansion (CTE) of the dental core with that of a dental veneer (or a portion of the dental veneer). Otherwise, in some cases, the veneer and the core may not be fused correctly during firing which might lead to failure of the restoration. In some embodiments, glass itself (e.g., including some of the formulations listed above) may match that of zirconia. In some embodiments, for example, when a dental core comprises alumina and/or metal, which tend to have a higher CTE, a crystalline material (e.g., leucite) may need to be added to the glass forming the veneer. Adding leucite to glass can raise the CTE of the glass, and can also improve the mechanical strength of the glass, but crystal materials other than leucite can also be used. The amount of leucite (or other crystal phase) to be added to the glass can depend on the material makeup of the dental core to which the dental veneer will be coupled (e.g., fused), because different metals and alloys have different CTEs. Table 1 lists exemplary pairings of dental core and dental veneer materials. Table 1 is only intended to be illustrative and not limiting:

TABLE 1

Exemplary pairings of dental core and dental veneer materials

| Dental Core materials | Dental Veneer materials |
|---|---|
| Zirconia | glass (e.g., SiO2 with Al2O3, K2O, Na2O, etc.) |
| Alumina | glass ceramic: glass fraction (e.g., SiO2 with Al2O3, K2O, Na2O, etc.) and crystalline fraction (e.g. leucite) |
| Metal | glass ceramic: glass fraction (e.g., SiO2 with Al2O3, K2O, Na2O, etc.) and crystalline fraction (e.g. leucite) |

The term "glass" generally refers to a hard, brittle, transparent solid. Examples of glasses can include, but are not limited to, soda-lime glass and borosilicate glass. A glass can include an inorganic product of fusion that has been cooled to a rigid condition without crystallizing. Some glasses contain silica as their main component and a certain amount of glass former.

The phrase "glass ceramic" generally refers to a material sharing many properties with both glass and more traditional crystalline ceramics. It is formed as a glass, and then made to crystallize partly by heat treatment. Unlike sintered ceramics, glass-ceramics have no pores between crystals. Instead, the space between the crystallites is filled by the glassy matrix. Glass ceramics mainly refer to a mixture of alkali metal-, silicon-, and aluminium-oxides.

The term "ceramic" generally refers to an inorganic nonmetallic material that can be produced by application of heat. Ceramics can be hard, porous and brittle and, in contrast to glasses or glass ceramics, can display an essentially purely crystalline structure.

A dental ceramic appliance can be classified as "pre-sintered" within the meaning of the present disclosure if the dental ceramic appliance has been treated with heat (e.g., a temperature ranging from about 900 to about 1100° C.) for about 1 to about 3 hours to such an extent that the raw breaking resistance (Weibull strength Sigma 0) of the dental ceramic appliance is within a range of about 15 to about 55 MPa or about 30 to about 50 MPa (measured according to the "punch on three ball test" (biaxial flexural strength) described in DIN EN ISO 6872, edition March 1999, with the following modifications: diameter of steel ball: 6 mm; diameter of support circle: 14 mm; diameter of flat punch: 3.6 mm; diameter of sample disc: 25 mm, thickness of sample disc: 2 mm; no grinding and polishing of samples).

A pre-sintered dental ceramic appliance can include a porous structure and its density (e.g., which can be 3.0 g/cm$^3$ for an Yttrium stabilized $ZrO_2$ ceramic) can be less compared to a completely sintered or finally sintered (or "finely sintered"; i.e., such that there will be no further sintering step) dental ceramic appliance (e.g., which can be 6.1 g/cm$^3$ for an Yttrium stabilized $ZrO_2$ ceramic). In some embodiments, the diameter of the pores can be in a range of about 50 nm to about 150 nm (corresponding to about 500 to about 1500 Å). In some embodiments, a pore diameter can be about 120 nm.

In some embodiments, pre-sintering of a glass and/or glass ceramic material can be effected in a temperature range of about 500 to about 750° C.

The term "sintering" generally refers to making objects from a powder by heating the material (e.g., below its melting point—"solid state sintering") until its particles adhere to each other. Sintering can cause the densification of a porous material to a less porous material (or a material having less cells) having a higher density. In some cases, sintering can also include changes of the material phase composition (e.g., a partial conversion of an amorphous phase toward a crystalline phase).

The terms "sintering" and "firing" are used interchangeably herein. A pre-sintered ceramic framework can shrink during a sintering step, that is, if an adequate temperature is applied. The sintering temperature to be applied depends on the ceramic material chosen. For example, for $ZrO_2$-based ceramics, a sintering temperature can range from about 1200° C. to about 1500° C. In some embodiments, $Al_2O_3$-based ceramics can be sintered at a temperature ranging from about 1300° C. to about 1700° C. In some embodiments, glass ceramic materials can be sintered at a temperature ranging from about 700 to about 1100° C. for about 1 to about 3 hours. In some embodiments, a firing step of the present disclosure can include firing at a temperature of at least about 500° C., in some embodiments, at least about 700° C., in some embodiments, at least about 1000° C., and in some embodiments, at least about 1200° C.

The unit "cells per $mm^2$" is related to the number of cells present on a cross section of the sample to be analysed. A suitable test method is given in DIN 13925.

The term "casting" generally refers to a manufacturing process by which a liquid material (e.g. solution or dispersion) is poured into a mold, which contains a hollow cavity (i.e., negative) of the desired shape, and then allowed to solidify.

A "sol-gel reaction" is a wet-chemical technique (sometimes also referred to as "Chemical Solution Deposition") for the fabrication of materials starting either from a chemical solution or colloidal particles (e.g. nanoscale particle) to produce an integrated network (gel). In some embodiments, sol-gel precursors can include metal alkoxides and metal chlorides, which undergo hydrolysis and polycondensation reactions to form a colloid, a system composed of solid particles (e.g., with sizes ranging from 1 nm to 1 μm) dispersed in a solvent. The sol can then evolve toward the formation of an inorganic continuous network containing a liquid phase (gel). Formation of a metal oxide can include connecting the metal centers with oxo (M-O-M) or hydroxo (M-OH-M) bridges, therefore generating metal-oxo or metal-hydroxo polymers in solution. A drying process can serve to remove the liquid phase from the gel thus forming a porous material. Afterwards, a thermal treatment (e.g., firing) may be performed in order to favor further polycondensation and enhance mechanical properties.

The phrase "porous material" can generally refer to a material comprising a partial volume that is formed by voids, pores, or cells in the technical field of ceramics.

A "liquid" is any solvent or liquid which is able to at least partially disperse or dissolve an inorganic binder of a slurry or mixture composition at ambient conditions (e.g. 23° C., 1013 mbar).

A composition or solution is "essentially or substantially free of" a certain component within the meaning of the present disclosure if the composition or solution does not contain said component as an essential feature. That is, such a component is not wilfully added to the composition or solution either as such or in combination with other components or as an ingredient of other components. In some embodiments, a composition being essentially free of a certain component usually contains the component in an amount of less than about 1 wt.-%, in some embodiments less than about 0.1 wt.-%, in some embodiments less than about 0.01 wt.-%, and in some embodiments less than about 0.001 wt.-%, with respect to the whole composition. In some embodiments, "essentially or substantially free of" generally refers to the composition or solution not containing the component at all. However, sometimes the presence of a small amount of the component may not be avoidable, e.g. due to impurities being present in the raw materials used.

As mentioned above, some systems and methods of the present disclosure provide individually shaped, layered dental appliances with complex shapes relatively quickly using a gel casting process. In some embodiments, a sol-gel casting process is employed in which a slurry or mixture is formed by combining:

(i) a glass and/or glass ceramic powder;
(ii) a liquid (e.g., water);
(iii) a binder (e.g., an inorganic binder); and
(iv) an activator (e.g., an acid or base).

In some embodiments, the slurry comprises components (i), (ii) and (iii), and the activator (component (iv)) is not added until just prior to casting.

By providing a mixture comprising a liquid, a binder (e.g., an inorganic binder), and glass and/or glass ceramic powder or particles, a sol-gel process can be initiated resulting in a homogeneous distribution of the glass and/or glass ceramic powder or particles in an inorganic network. In contrast to this, blocks produced by uniaxial pressing sometimes are inhomogeneous with regard to density. This may be caused by an inhomogeneous pressure distribution in the pressing matrix.

Compared to a dental appliance manufactured by a pressing process and having insufficient strength unless it is pre-sintered, the dental appliance obtainable according to the gel casting process of the present disclosure has sufficient strength and can be machined without pre-sintering the dental appliance beforehand.

Moreover, machining is not limited to grinding only but can also be accomplished by milling as well. As outlined above, the strength of the dental appliance is high enough that the dental appliance can be machined without a sintering step, but low enough that the dental appliance can be shaped by applying the more efficient (e.g. faster and cheaper) milling process.

Furthermore, by using an inorganic binder for creating an inorganic network instead of an organic binder, there are less exhaust gases evaporating from the dental appliance during a later heating or sintering step. Organic binders typically produce gases like carbon and/or nitrogen oxides. Examples of inorganic binders according to the present disclosure, if at all, only produce low boiling solvents like alcohols (e.g. methanol and ethanol) which typically evaporate during the drying step.

In addition and in contrast to pressing techniques which can be limited to specific shapes (e.g., cube and cylinder), the casting process of the present disclosure facilitates the manufacturing of complex shapes. The shape of the obtained dental appliance is only limited to the shape of the mold used. Thus, objects with convex and/or concave structures can be manufactured.

Compared to pre-sintered dental appliances, the dental appliances obtained by the process of the present disclosure can have a lower density. The lower density can facilitate machining of the dental appliance (e.g. extended service life of machining tools), and can also reduce the amount of waste that is produced during the shaping process.

Some methods of the present disclosure facilitate providing colored dental appliances. Coloring additives can be added very early in the process (e.g. when the mixture to be casted is provided) and/or later on in the process (e.g. after the drying step). If the coloring is to be done after the drying step, it can be done by using a coloring solution containing coloring additives (e.g. metal salts).

Adding coloring additives at an early stage in the process, for example when providing the mixture to be casted, can result in a homogenous distribution of the coloring additives throughout the resulting dental appliance, or throughout a layer of the resulting layered dental appliance.

The amount of inorganic binder precursor used can allow for adjusting or influencing the gel time and block toughness. The amount of powder and water used can also allow for adjusting the density of the dried blocks.

FIG. 1 illustrates a schematic flowchart of a method 10 according to one embodiment of the present disclosure and a system 50 according to one embodiment of the present disclosure. The illustrated method 10 includes steps 10A-10H, and the system 50 includes a mold 52, and can further include a dental core 54 dimensioned to be at least partially received in the mold 52 and used to form the innermost center or core of the desired layered dental appliance. The system 50 can further include one or more slurries, as described in greater detail below.

In some embodiments, the system 50 can include a mold assembly that comprises the base mold (or "negative" mold) 52 shown in FIG. 1 and another mold portion used to hold the dental core 54 during formation of the layers on the dental core 54. That is, in some embodiments, the mold 52 shown in FIG. 1 can be one portion or one half of a mold, and an additional portion can be used to hold the dental core 54. For simplicity, only the bottom portion (e.g., the "negative" portion) of such a mold is shown in FIG. 1 and described below, but it should be understood that a variety of means for holding and inserting the dental core 54 (and subsequent articles comprising the dental core 54) into the mold 52 shown in FIG. 1 can be employed, such as the two-part mold described in Example 1. However, it should also be understood that in some embodiments, only the base mold 52 is employed and another means for holding and inserting the dental core 54 is employed.

In some embodiments, the system 50 itself can be described as a mold system or assembly that includes a first portion 52 comprising a negative of an outer shape (e.g., of a first layer) of the desired dental appliance, and a second portion comprising the dental core 54.

In the exemplary method 10 illustrated in FIG. 1, steps 10A-10H result in a two-layer dental appliance (three-layer dental appliance if the dental core is considered a layer). Steps 10A-10D are used to form a first article 63 comprising a first layer 65 positioned on the dental core 54, and steps 10E-10H are used to form a second article 73 comprising a second layer 75 positioned on the first article 63. In the exemplary method 10, steps 10E-10H are substantially similar to steps 10A-10D, and steps 10A-10D represent one iteration of forming a layer in the method 10, while steps 10D-10H represent another iteration of forming a layer in the method 10. That is, in the method 10 illustrated in FIG. 1, the first iteration (i.e., steps 10A-10D) is used to form a first innermost layer on the dental core 54, and the second iteration (i.e., steps 10E-10H) is used to form a second layer 75 that is positioned outwardly with respect to the first layer 65. As a result of the iterative nature of the method 10 shown in FIG. 1, it should be understood that any description of the elements, features and steps described with respect to steps 10A-10D (and alternatives to such elements, features and steps) also generally apply to steps 10E-10H, and vice versa. It should also be understood that the iterative steps can be repeated to achieve a layered dental appliance having as many layers as desired.

In a first step 10A of the method 10, the mold 52 provided. The mold 52 can be adapted to receive one or more slurries, dimensioned to receive at least a portion of the dental core 54, and can include a negative shape or surface (or cavity) 58 of the outer shape (or outer layer) of the desired dental appliance.

In some embodiments, the mold 52 (or a mold assembly comprising one or more parts of a multi-part mold) can be characterized by at least one of the following features:
volume of the mold: can be less than about 1 $cm^3$ or can be above about 20 $cm^3$;
useful ranges include 0.2 $cm^3$ to about 50 $cm^3$, or about 0.5 $cm^3$ to about 30 $cm^3$;
dimensions of the mold: arbitrary, as long as there are no cavities too small to be filled by the reaction mixture;
shape of the mold: arbitrary, as long as there are no cavities too small to be filled by the reaction mixture; and/or
examples of materials of the mold: silicone, polyethylene (PE), polypropylene (PP), polycarbonate, polyurethane, polystyrene, polyoxymethylene, other suitable polymers, metal (e.g. steel), etc., or combinations thereof.

In some embodiments, the mold 52 can have a regular (e.g., cubic, cylindrical, etc.) or irregular shape (e.g., shape of a tooth, veneer, inlay, onlay, crown, bridge, orthodontic bracket, other suitable dental appliance shapes, etc., or combinations thereof). For example, a "simple, tooth-like" shape can be used for near-net shape applications. In some embodiments, a mold having a specially designed tooth-shape can be used for net-shape applications. By way of example, in some embodiments, a specially designed tooth-shape (e.g., a positive of the tooth-shape and/or a negative of the tooth-shape) can be produced by a digital workflow, and a negative can be used as the mold or a positive can be used to form the mold. Such a digital workflow can include scanning a patient's mouth to develop a model for the desired dental appliance. Such scanning can be performed using an optical scanner that is coupled to a computer-aided design (CAD) system that functions in conjunction with a computer-integrated manufacturing (CIM) system. Such a CIM system is available, for example, under the trade designation LAVA™ from 3M ESPE AG (Seefeld, Germany).

In some embodiments, at least a portion of the mold 52 can be enlarged relative to the desired resulting dental appliance, for example, to accommodate for any shrinkage that may occur (e.g., when the dental appliance is fired). For example, in some embodiments, at least a portion of the mold 52 can be at least 110% of the size of the resulting appliance, in some embodiments, at least 150%, and in some embodiments, at least 200%.

In some embodiments, the enlargement of the mold 52 can be accomplished via computer assisted design and manufacturing (CAD/CAM), for example, by milling or printing a wax model, embedding it in a mold material and burning the wax after casting. Alternatively, in some embodiments, the mold can be milled, wax- or 3D-printed, formed by rapid prototyping, formed by stereolithography, or a combination thereof. In addition, in some embodiments, the enlargement can be accomplished via copy milling or other hand driven enlargements, e.g., by coating a hand-made wax-up with a layer of a certain thickness that corresponds to the desired percent enlargement.

In some embodiments, the mold 52 can include a holder (e.g., adapted to hold the dental core 54 and/or be embedded into the mold 52). That is, in some embodiments, the dental appliance after having been removed from the mold 52 can contain a holder or can be fixed to a holder. This can facilitate handling of the dental appliance in a further processing or machining step. In some embodiments, the holder can be formed of metal.

As shown in FIG. 1, in the first step 10A of the method 10, a first slurry 62 can be positioned (e.g., cast) in the mold 52. In addition, the dental core 54 can begin being moved toward or into the interior of the mold 52. The dental core 54 can include an outer surface 60. By way of example only, the dental core 54 is shown in FIG. 1 as fitting concentrically/axially and symmetrically in the mold 52; however, it should be understood that the dental core 54 can instead be positioned "off-center" with respect to the mold 52, and can mate or cooperate with the mold 52 in a variety of ways.

In some embodiments, any casting step of the present disclosure can be characterized by at least one of the following features:
 duration: about 2 to about 5 seconds for 10 g of reaction mixture; and/or
 temperature: about 10 to about 40° C. or about 15 to about 30° C. or at ambient conditions (i.e., ambient temperature and pressure, e.g., 23° C., 1013 mbar).

In some embodiments, reducing the formation of air bubbles during the casting step can be avoided, for example, by applying reduced pressure.

In some embodiments, the casting step can be more robust and useful than other molding procedures, such as injection molding, which can require precise control over processing temperatures, and/or the viscosity of the material being molded, at various stages throughout the molding process. On the contrary, an inorganic casting procedure (e.g., sol-gel casting) of the present disclosure can facilitate filling narrow cavities to achieve a desired shape, and can include forming the desired shape and material via a chemically-controlled process, rather than a potentially unforgiving temperature-controlled process, which can require expensive technological equipment. In addition, other molding procedures, such as injection molding, employ higher pressures (e.g., higher than ambient pressures), and can require precise control and maintenance of various pressures as well.

As mentioned above, the first slurry 62 can include (i) a glass and/or glass ceramic powder; (ii) a liquid (e.g., water); (iii) a binder (e.g., an inorganic binder); and (iv) an activator (e.g., an acid or base). The formulation of the slurries of the present disclosure and exemplary methods of forming the slurries of the present disclosure are described in greater detail below. The slurries of the present disclosure can sometimes be referred to as "glass and/or glass ceramic" slurries.

In a second step 10B of the method 10, the dental core 54 can be pressed into the first slurry 62, forming the first article 63 comprising the dental core 54 and the first layer 65. The term "article" is used by way of example only to indicate any article as defined above, but it should be understood that a variety of other terms, such as "appliance," "construction," "intermediate," or the like, could instead be used to describe the form resulting from forming the first layer 65 on the dental core 54. The first article 63 can then be dried to allow for the first layer 65 to harden on the dental core 54. That is, the entire construction comprising the mold 52, the dental core 54, and the first slurry 62 pressed between the mold 52 and the dental core 54 can be dried (e.g., at ambient conditions and/or in a drying oven at an elevated temperature) to harden the first slurry 62 and form the first layer 65 (and the first article 63).

Any drying step of the present disclosure can be characterized by at least one of the following features:
 duration: up to about 24 h or up to about 8 h or up to about 1 h,
 temperature: from about 10 to about 120° C. or about 20 to about 100° C., and/or
 pressure: ambient pressure.

During the drying step, the network-formation of the binder can be finalized and low boiling components that may have been generated during the network forming process, if any, can evaporate from the cast mixture.

Drying can be performed at ambient conditions by simply letting the mold containing the mixture stand for a sufficient period of time. If a more rapid drying is desired, drying can be performed in a drying oven.

As shown in a third step 10C of the method 10, the first article 63 can be removed from the mold 52. The first article 63 can then be fired to form a fired first article 63' comprising a fired first layer 65' and the dental core 54, as shown in step 10D. In some embodiments, in the firing step, additional sintering of the dental core 54 and/or shrinkage of the first layer 65 can occur. As shown in FIG. 1, the fired first layer 65' takes up less volume (and is thinner) than the unfired first layer 65 shown in steps 10B and 10C. As such, the fired first article 63' can be dimensioned to be received in the mold 52.

A firing or sintering step of the present disclosure can be characterized by at least one of the following features:
 duration: about 10 to about 60 min or about 20 to about 25 min,
 temperature: about 600 to about 900° C. or about 750 to about 850° C.,
 pressure: about 10 to about 50 mbar or about 15 to about 35 mbar, and/or
 atmosphere: air.

Sintering can be conducted in a commercially available sinter furnace (e.g. Austromat 3001 from Dekema Comp.; Germany).

Sintering, if at all, can be conducted before the resulting dental appliance is machined or afterwards. In some embodiments when sintering is employed, the sintered material can have a density in a range of about 2 g/cm$^3$ to about 2.7 g/cm$^3$.

The sintered material can include a level of translucency. The translucency can be specified by the opacity of a material relative to daylight. In some embodiments, the opacity of the sintered material ranges from about 50% to about 60% (e.g., corresponding to natural dental enamel), in some embodiments from about 60% to about 80% (e.g., corresponding to natural dentine), and in some embodiments from about 80% to about 90% (e.g., corresponding to natural opaque dentine).

In some embodiments, the desired dental appliance can include only one layer formed over the dental core 54. In such embodiments, the method 10 can include steps 10A-10D only, and the layered dental appliance can include the fired first article 63' (or the first article 63). The fired first article 63' (or the first article 63) can optionally be further fired (e.g., under a vacuum) and/or machined.

A machining step of the present disclosure can be characterized by at least one of the following features:
 machining can be accomplished under dry or wet conditions,
 milling parameter rotation: about 18,000 to about 32,000 rpm, and/or
 milling parameter motion: about 1,500 to about 2,500 mm per minute.

Other machining equipment as those mentioned in the above definition of machining can be used, if desired.

As shown in FIG. 1, in a third step 10C of the method 10, the first article 63 can be removed from the mold 52, leaving behind the open mold 52 (e.g., the inner (negative) surface 58 of the mold 52). In some embodiments, the same mold 52 can be reused for subsequent casting of additional layers. For example, in some embodiments, the mold 52 can be cleaned and reused. In some embodiments, another mold 52 having the same dimensions as the original mold 52 can be used for the next subsequent casting step(s). In some embodiments, the same mold 52 can be used for two or more casting steps, and in some embodiments, a different mold 52 (but having the same inner dimensions and same inner (negative) surface 58) can be used for each casting step.

In a fifth step 10E of the method, a second slurry 72 is positioned (e.g., cast) in the mold 52. In addition, the fired first article 63' can begin being moved toward or into the interior of the cavity 58 in the mold 52. The fired first article 63' can include an outer surface 70.

Similar to the first slurry 62, the second slurry 72 can include (i) a glass and/or glass ceramic powder; (ii) a liquid (e.g., water); (iii) a binder (e.g., an inorganic binder); and (iv) an activator (e.g., an acid or base). The second slurry 72 can be the same formulation or a different formation as the first slurry 62.

In a sixth step 10F of the method 10 illustrated in FIG. 1, the fired first article 63' can be pressed into the second slurry 72, forming the second article 73 comprising the fired first article 63' and the second layer 75 of the dental appliance. Said another way, the second article 73 can include the dental core 54, the first layer 65, and the second layer 75. Again, the term "article" is used by way of example only to indicate any article as defined above, but it should be understood that a variety of other terms, such as "appliance," "construction," "intermediate," or the like, could instead be used to describe the form resulting from forming the second layer 75 on the first article 63 (i.e., on the fired first article 63'). The second article 73 can then be dried to allow for the second layer 75 to harden. That is, the entire construction comprising the mold 52, the fired first article 63', and the second slurry 72 pressed between the mold 52 and the fired first article 63' can be dried (e.g., at ambient conditions and/or in a drying oven at an elevated temperature) to harden the second slurry 72 and form the second layer 75 (and the second article 73).

In some embodiments, the first layer 65 can have the greatest thickness. For example, in some embodiments, the fired first article 63' can take up a larger volume than the original dental core 54. In such embodiments, there can be less volume or space available for forming the second layer 75 of the dental appliance than there was for forming the first layer 65. Having less space available for forming the second layer 75 can result in the second layer 75 being thinner than the first layer 65. That is, in some embodiments, the layers of the resulting layered dental appliance can decrease from the innermost layer to the outermost layer (or can increase toward the dental core 54). Alternatively, in some embodiments, the layers can increase in thickness from the innermost layer to the outermost layer (or can decrease toward the dental core 54). For example, such embodiments can be achieved by employing different slurries that shrink differently during firing.

As shown in FIG. 1, in a seventh step 10G of the method 10, the second article 73 can be removed from the mold 52. The second article 73 can then be fired to form a fired second article 73' comprising the dental core 54, the fired first layer 65', and a fired second layer 75', as shown in step 10H. In some embodiments, in the firing step, additional sintering of the dental core 54 and/or shrinkage of the first layer 65 can occur. In addition, shrinkage of the second layer 75 can occur. As shown in FIG. 1, the fired second layer 75' takes up less volume (and is thinner) than the unfired second layer 75 shown in steps 10F and 10G. As such, in some embodiments, the fired second article 73' can be dimensioned to be received in the mold 52 for additional layers, as necessary.

In the embodiment of the method 10 and system 50 shown in FIG. 1, the fired second article 73' forms the resulting layered dental appliance. The fired second article 73' (or the second article 73) can optionally be further fired (e.g., under a vacuum) and/or machined.

However, it should be understood that the method 10 can continue iteratively forming additional layers to achieve a layered dental appliance having the desired number of layers coupled (e.g., fused) to the dental core 54. That is, in some embodiments, the resulting layered dental appliance can include a dental veneer formed by the above described systems and methods comprising any desired number of layers (e.g., the first layer 65 (or fired first layer 65') and/or the second layer 75 (or fired second layer 75') that is coupled to (e.g., fused) to the dental core 54.

In some embodiments, the resulting dental appliance (e.g., the fired second article 73'), or one or more layers of the dental appliance, may be substantially free of cells, voids or pores, or can include up to about 20 cells per $mm^2$. In some embodiments, the dental appliance, or one or more layers of the dental appliance can include about 4 to about 10 cells per $mm^2$. In some embodiments, the cells can have a diameter of less than about 150 μm, in some embodiments less than about 100 μm, and in some embodiments less than about 50 μm.

In some embodiments, the volume of the cells in the dental appliance (or one or more layers of the dental appliance), relative to the total volume of the dental appliance (or relative to the total volume of the one or more layers of the dental appliance) can range from about 20% to about 40%, and in some embodiments can range from about 30% to about 38%. In some embodiments, these percentages refer to a pre-sintered state, not to a fully sintered glass or glass ceramic.

As can be understood by the above description of the method 10 and the system 50 of FIG. 1 and alternatives to the method 10 and the system 50, the present disclosure provides a multilayer dental appliance having two or more layers, wherein the innermost layer can include a dental core. Furthermore, the method 10 is shown by way of example only as including two casting steps. However, it should be understood that as many casting steps as necessary can be employed to form a layered dental appliance having a desired number of layers.

In addition, in the description above, the final dental appliance and the method 10 used to make the dental appliance are described as including and forming a first layer 65 and a second layer 75 on the dental core 54. However, in some embodiments, the final dental appliance can include many layers, and the method 10 for making the dental appliance can include many repetitions of steps 10E-10H. In such embodiments, the method can be iterative, and the innermost layer can be referred to as "layer n-(n−1)," the next successive (outer) layer can be referred to as "layer n-(n−2)," the next successive (outer) layer can be referred to as "layer n-(n−3)," and so on. In other words, each layer x, which runs from 1 to n (from the innermost layer to the outermost layer), can be referred to as "layer n-(n−x)," or each layer can be referred to as "layer n−x," where x runs from 0 to n−1 (from the outermost layer to the innermost layer). Said another way, the innermost layer can be referred to as "layer 1," the next successive (outer) layer can be referred to as "layer 2," the next successive (outer) layer can be referred to as "layer 3," and so on, and the final outermost layer can be referred to as "layer n," where the resulting layered dental appliance includes n layers.

In addition, by way of example only and for simplicity of illustration, the dental core 54 is shown as being pressed into the first and second slurries 62 and 72, respectively, until the dental core 54 is flush with the top surfaces of the mold 52. However, the schematic shapes of the parts shown in FIG. 1 and the cooperation between such parts are shown in FIG. 1 by way of example only and for purposes of illustration, and are not intended to be limiting. In addition, in some embodiments, the dental core 54 may not be pressed so far into the mold 52. In some embodiments, excess of one or more of the slurries 62 and/or 72 can be forced out of the mold 52 when the dental core 54 is moved into the mold 52. Such excess may need to be removed during downstream processing (e.g., machining).

Figure 2:
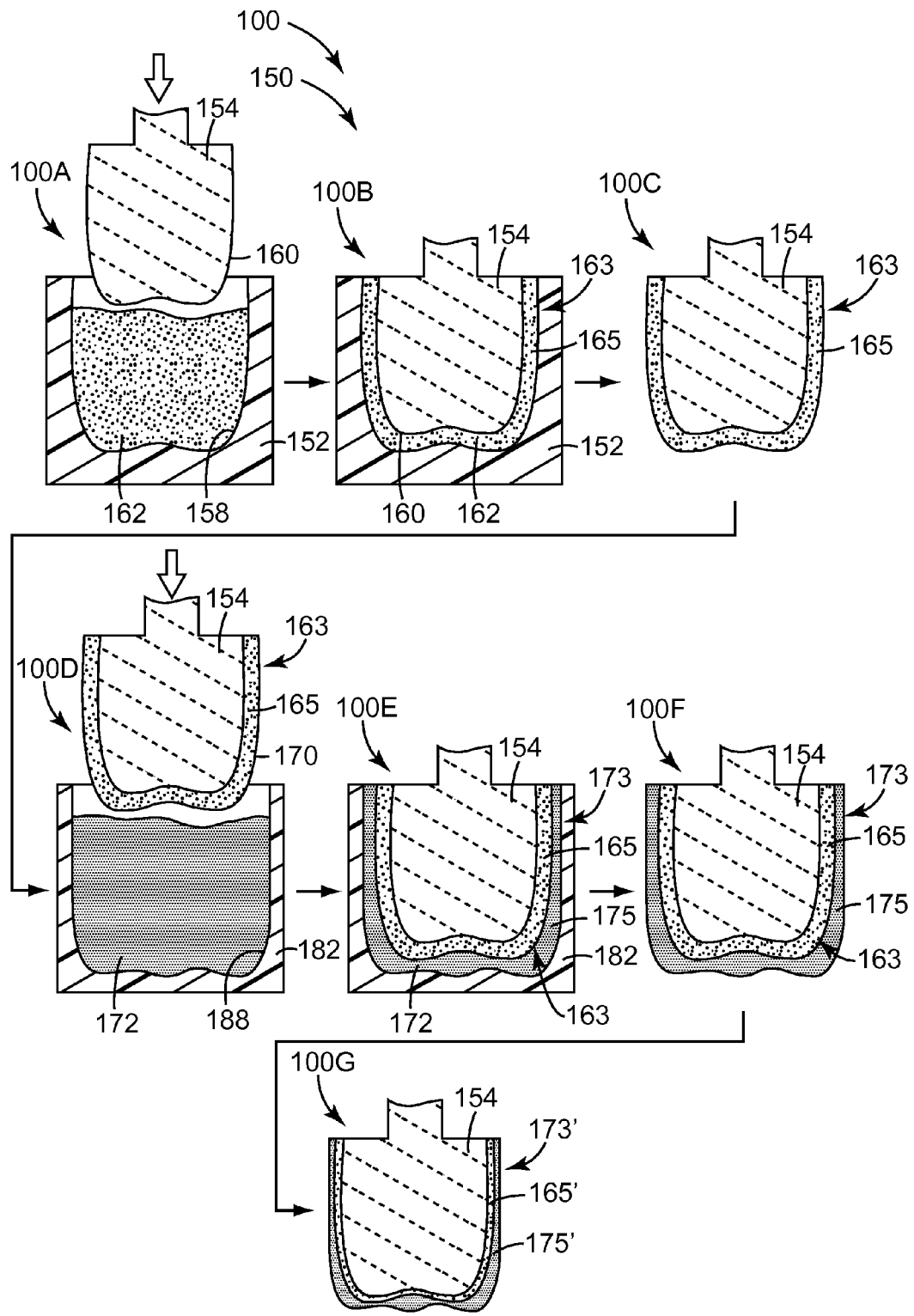
FIG. 2 is a schematic flowchart of a method according to another embodiment of the present disclosure and illustrates a system according to another embodiment of the present disclosure.

FIG. 2 illustrates another method 100 according to another embodiment of the present disclosure and a system 150 according to another embodiment of the present disclosure, wherein like numerals represent like elements. The method 100 and system 150 share many of the same elements and features described above with reference to the illustrated embodiments of FIG. 1. Accordingly, elements and features corresponding to elements and features in the illustrated embodiments of FIG. 1 are provided with the same reference numerals in the 100 series. Reference is made to the description above accompanying FIG. 1 for a more complete description of the features and elements (and alternatives to such features and elements) of the method 100 and system 150 illustrated in FIG. 2.

The illustrated method 100 includes steps 100A-100G, and the system 150 includes a first mold 152, a second mold 182, and can further include a dental core 154 dimensioned to be at least partially received in the first mold 152 and the second mold 182, and used to form the innermost center or core of the desired layered dental appliance. The system 150 can further include one or more slurries, as described in greater detail below. It should be understood that any description above of the features and elements (and alternatives to such features and elements) of the mold 52 of FIG. 1 applies equally to both the first mold 152 and the second mold 182 of the embodiment illustrated in FIG. 2.

In the exemplary method 100 illustrated in FIG. 2, steps 100A-100G result in a two-layer dental appliance (three-layer dental appliance if the dental core is considered a layer). Steps 100A-100C are used to form a first article 163 comprising a first layer 165 positioned on the dental core 154, and steps 100D-100F are used to form a second article 173 comprising a second layer 175 positioned on the first article 163. In the exemplary method 100, steps 100D-100F are substantially similar to steps 100A-100C, and steps 100A-100C represent one iteration of forming a layer in the method 100, while steps 100D-100F represent another iteration of forming a layer in the method 100. That is, in the method 100 illustrated in FIG. 2, the first iteration (i.e., steps 100A-100C) is used to form a first innermost layer 165 on the dental core 154, and the second iteration (i.e., steps 100D-100F) is used to form a second layer 175 that is positioned outwardly with respect to the first layer 165. As a result of the iterative nature of the method 100 shown in FIG. 2, it should be understood that any description of the elements, features and steps described with respect to steps 100A-100C (and alternatives to such elements, features and steps) also generally apply to steps 100D-100F, and vice versa. It should also be understood that the iterative steps can be repeated to achieve a layered dental appliance having as many layers as desired.

In a first step 100A of the method 100, the first mold 152 provided. The first mold 152 can be adapted to receive one or more slurries, dimensioned to receive at least a portion of the dental core 154, and can include a negative shape or surface (or cavity) 158 of the first layer 165 of the desired dental appliance.

In some embodiments, at least a portion of the first mold 152 can be enlarged relative to the desired resulting dental appliance (or first article 163), for example, to accommodate for any shrinkage that may occur (e.g., when the dental appliance (or any intermediate thereof, such as the first article 163) is fired). For example, in some embodiments, at least a portion of the first mold 152 can be at least 110% of the size of the resulting appliance, in some embodiments, at least 150%, and in some embodiments, at least 200%.

As shown in FIG. 2, in the first step 100A of the method 100, a first slurry 162 can be positioned (e.g., cast) in the first mold 152. In addition, the dental core 154 can begin being moved toward or into the interior of the first mold 152. The dental core 154 can include an outer surface 160.

As mentioned above, the first slurry 162 can include (i) a glass and/or glass ceramic powder; (ii) a liquid (e.g., water); (iii) a binder (e.g., an inorganic binder); and (iv) an activator (e.g., an acid or base). The formulation of the slurries of the present disclosure and exemplary methods of forming the slurries of the present disclosure are described in greater detail below. The slurries of the present disclosure can sometimes be referred to as "glass and/or glass ceramic" slurries.

In a second step 100B of the method 100, the dental core 154 can be pressed into the first slurry 162, forming the first article 163 comprising the dental core 154 and the first layer 165. The term "article" is used by way of example only to indicate any article as defined above, but it should be understood that a variety of other terms, such as "appliance," "construction," "intermediate," or the like, could instead be used to describe the form resulting from forming the first layer 165 on the dental core 154. The first article 163 can then be dried and/or the first layer 165 can be allowed to harden on the dental core 154. That is, the entire construction comprising the first mold 152, the dental core 154, and the first slurry 162 pressed between the first mold 152 and the dental core 154 can be dried (e.g., at ambient conditions and/or in a drying oven at an elevated temperature) to harden the first slurry 162 and form the first layer 165 (and the first article 163).

As shown in a third step 100C of the method 100, the first article 163 can be removed from the first mold 152. In some embodiments, the desired dental appliance can include only one layer formed over the dental core 154. In such embodiments, the method 100 can include steps 100A-100C only, and the layered dental appliance can include the first article 163, or the first article 163 can optionally be fired, and/or machined.

As shown in FIG. 2, in a fourth step 100D of the method 100, a second mold 182 is provided. The second mold 182 can be adapted to receive one or more slurries, dimensioned to receive at least a portion of the dental core 154, and can include a negative shape or surface (or cavity) 188 of the second layer 175 of the desired dental appliance. By way of example only, the second mold 182 is illustrated as having a different inner shape or cavity 188 than the cavity 158 of the first mold 152, such that the second layer 175 and the first layer 165 can have different shapes or configurations, for example, for aesthetics, function, etc. For example, in some embodiments, the first layering step (100A-100C) and the first mold 152 can be specially designed to mold the first layer 165 representing a dentin structure (or a structure that mimics dentin). By way of further example, the second layering step (100D-100F) and the second mold 182 can be specially designed to mold the second layer 175 representing an enamel structure (or a structure that mimics enamel). In such embodiments, a special dentin mold can be useful for creating real anatomical shaping of individual layers (e.g., for anterior teeth). In addition, in such embodiments, the second mold 182, or at least the cavity 188 of the second mold 182, can be larger than the first mold 152, or the cavity 158 of the first mold 152, to accommodate for the dental core 154 and the first layer 165.

In some embodiments, at least a portion of the second mold 182 can be enlarged relative to the desired resulting dental appliance (or second article 173), for example, to accommodate for any shrinkage that may occur (e.g., when the dental appliance (or any intermediate thereof, such as the second article 173) is fired). For example, in some embodiments, at least a portion of the second mold 182 can be at least 110% of the size of the resulting appliance, in some embodiments, at least 150%, and in some embodiments, at least 200%.

As further shown in step 100D of the method 100 of FIG. 2, a second slurry 172 can be positioned (e.g., cast) in the second mold 182. In addition, the first article 163 can begin being moved toward or into the interior of the cavity 188 in the second mold 182. The first article 163 can include an outer surface 170.

Similar to the first slurry 162, the second slurry 172 can include (i) a glass and/or glass ceramic powder; (ii) a liquid (e.g., water); (iii) a binder (e.g., an inorganic binder); and (iv) an activator (e.g., an acid or base). The second slurry 172 can be the same formulation or a different formation as the first slurry 162.

In a fifth step 100E of the method 100 illustrated in FIG. 2, the first article 163 can be pressed into the second slurry 172, forming the second article 173 comprising the first article 163 and the second layer 175 of the dental appliance. Said another way, the second article 173 can include the dental core 154, the first layer 165, and the second layer 175. Again, the term "article" is used by way of example only to indicate any article as defined above, but it should be understood that a variety of other terms, such as "appliance," "construction," "intermediate," or the like, could instead be used to describe the form resulting from forming the second layer 175 on the first article 163. The second article 173 can then be dried to allow for the second layer 175 to harden. That is, the entire construction comprising the second mold 182, the first article 163, and the second slurry 172 pressed between the second mold 182 and the first article 163 can be dried (e.g., at ambient conditions and/or in a drying oven at an elevated temperature) to harden the second slurry 172 and form the second layer 175 (and the second article 173).

In some embodiments, the first layer 165 can have the greatest thickness. For example, in some embodiments, the first article 163 can take up a larger volume in the second mold 182 than the original dental core 154 took up in the first mold 152. In such embodiments, there can be less volume or space available for forming the second layer 175 of the dental appliance than there was for forming the first layer 165. Having less space available for forming the second layer 175 can result in the second layer 175 being thinner than the first layer 165. That is, in some embodiments, the layers of the resulting layered dental appliance can decrease from the innermost layer to the outermost layer (or can increase toward the dental core 154). Alternatively, in some embodiments, the molds 152 and 182 can be configured such that the layers increase in thickness from the innermost layer to the outermost layer (or can decrease toward the dental core 154).

As shown in FIG. 2, in a sixth step 100F of the method 100, the second article 173 can be removed from the second mold 182. The second article 173 can then be fired to form a fired second article 173' comprising the dental core 154, a fired first layer 165', and a fired second layer 175', as shown in step 100G. In some embodiments, in the firing step, additional sintering and/or shrinkage of the dental core 154 can occur. In addition, shrinkage of the first layer 165 and/or the second layer 175 can occur. As shown in FIG. 2, the fired first layer 165' and the fired second layer 175' each take up less volume (and is thinner) than the unfired first layer 165 and the unfired second layer 175, respectively. As such, in some embodiments, the fired second article 173' can be dimensioned to be received in a third mold (not shown) for deposition of additional layers (e.g., a third layer formed from a third slurry), as necessary, and so on. Alternatively, in some embodiments, the steps 100D-100F can be repeated, such that the second article 173 (i.e., prior to any firing) can be dimensioned to be received in a third mold, and this iterative process can continue until desired, and the final article comprising the dried/hardened veneer layers on the dental core 154 can be fired to achieve the desired layered dental appliance.

In the embodiment of the method 100 and system 150 shown in FIG. 2, the fired second article 173' forms the resulting layered dental appliance. The fired second article 173' (or the second article 173) can optionally be further fired (e.g., under a vacuum) and/or machined.

However, it should be understood that the method 100 can continue iteratively forming additional layers to achieve a layered dental appliance having the desired number of layers coupled (e.g., fused) to the dental core 154. That is, in some embodiments, the resulting layered dental appliance can include a dental veneer formed by the above described systems and methods comprising any desired number of layers (e.g., the first layer 165 (or fired first layer 165') and/or the second layer 175 (or fired second layer 175') that is coupled to (e.g., fused) to the dental core 154.

As can be understood by the above description of the method 100 and the system 150 of FIG. 2 and alternatives to the method 100 and the system 150, the present disclosure provides a multilayer dental appliance having two or more layers, wherein the innermost layer can include a dental core. Furthermore, the method 100 is shown by way of example only as including two casting steps, performed in two different molds 152 and 182. However, it should be understood that as many casting steps, and as many molds, as necessary can be employed to form a layered dental appliance having a desired number of layers.

In addition, in the description above, the final dental appliance and the method 100 used to make the dental appliance are described as including and forming a first layer 165 and a second layer 175 on the dental core 154. However, in some embodiments, the final dental appliance can include many layers, and the method 100 for making the dental appliance can include many repetitions of steps 100D-100F. In such embodiments, the method can be iterative, and the innermost layer can be referred to as "layer n-(n−1)," the next successive (outer) layer can be referred to as "layer n-(n−2)," the next successive (outer) layer can be referred to as "layer n-(n−3)," and so on. That is, each layer x, which runs from 1 to n, can be referred to as "layer n-(n−x)."

In addition, by way of example only and for simplicity of illustration, the dental core 154 is shown as being pressed into the first and second slurries 162 and 172, respectively, until the dental core 154 is flush with the top surfaces of the first and second molds 152 and 182. However, the schematic shapes of the parts shown in FIG. 2 and the cooperation between such parts are shown in FIG. 2 by way of example only and for purposes of illustration, and are not intended to be limiting. In addition, in some embodiments, the dental core 154 may not be pressed so far into the molds 152 and 182. In some embodiments, excess of one or more of the slurries 162 and/or 172 can be forced out of one or more of the molds 152 and 182 when the dental core 154 is moved into the mold 152. Such excess may need to be removed during downstream processing (e.g., machining).

FIGS. 1 and 2 each illustrate an exemplary method 10, 100 and system 50, 150 of the present disclosure. However, it should be understood that various combinations of the steps employed in the methods 10 and 100 and/or various combinations of the systems 50 and 150 can also be employed. For example, in some embodiments, the method 10 and system 50 shown in FIG. 1 can be employed to form a fired second article 73' that can then be used to form a third layer with a different third mold, according to steps 100D-100G of the method 100 of FIG. 2 and the system 150 of FIG. 2. By way of further example, in some embodiments, the first article 163 of FIG. 2 can be fired prior to being pressed into the second slurry 172 in the second mold 182, similar to the firing step 10D of the method 10 shown in FIG. 1.

The following description of the formulation of the slurry and exemplary methods of forming one or more slurries of the present disclosure can generally apply to each of the first slurry 62, 152 and the second slurry 72, 172 shown in FIGS. 1 and 2, as well as to additional slurries that may be necessary in another embodiment of the method or system of the present disclosure. Other details and aspects regarding the mixture or slurry and inorganic gel casting of dental appliances can be found in EP Patent Application No. EP08165607.6, filed Oct. 1, 2008, entitled "Dental Appliance, Process for producing a dental appliance and Use thereof," the disclosure of which is incorporated herein by reference in its entirety.

Liquid

The nature and structure of the liquid to be used in a slurry of the present disclosure is not particularly limited, unless the intended purpose cannot be achieved.

In some embodiments, the liquid can be characterized by at least one of the following features:
 boiling point: about 60 to about 120° C.,
 freezing point: about −120 to about 0° C., and/or
 density: about 0.7 to about 1.2 g/cm$^3$.

Specific examples of liquids include, but are not limited to, water, alcohols (including methanol, ethanol n- and iso-propanol), ketones (including acetone), and combinations thereof.

In some embodiments, the liquid can be present in an amount ranging from about 15 wt.-% to about 60 wt.-%, in some embodiments from about 20 wt.-% to about 40 wt.-%, and in some embodiments from about 25 wt.-% to about 35 wt.-%, with respect to the whole composition or mixture, respectively.

In some embodiments, the liquid can be present in an amount of at least about 15 wt.-%, in some embodiments at least about 20 wt.-%, and in some embodiments at least about 25 wt.-%, with respect to the whole composition or mixture, respectively.

In some embodiments, the liquid can be present in an amount of no greater than about 35 wt.-%, in some embodiments no greater than about 40 wt.-%, and in some embodiments no greater than about 60 wt.-%, with respect to the whole composition or mixture, respectively.

Inorganic Binder

The nature and structure of the inorganic binder to be used in a slurry is not particularly limited, either, unless the intended purpose cannot be achieved.

The inorganic binder can form an inorganic network upon initiating a curing or hardening reaction. The curing or hardening reaction can be initiated e.g. by adjusting the pH value, either by adding acidic or basic reagents including those described in more detail below.

The network formed by the inorganic binder can have a similar or essentially identical chemical nature or composition as the chemical nature or composition of the glass/glass ceramic powder/particles used.

In some embodiments, the inorganic binder can be a liquid at ambient conditions (e.g., 23° C.; 1013 mbar) or applied as an aqueous solution and can be characterized by at least one of the following features:
 density: about 0.7 to about 1.5 g/cm$^3$ or about 0.9 to about 1.4 g/cm$^3$,
 molecular mass: about 100 to about 500 g/mol or about 150 to about 250 g/mol (for molecular precursors),
 containing Si and O, and/or
 producing low boiling by- or condensation products during hardening, if any (e.g. boiling point below about 120° C.).

Specific examples of inorganic binder precursors include, but are not limited to tetra alkyl (e.g. C1 to C4) orthosilicates (including tetramethyl orthosilicate (TMOS), tetraethyl orthosilicate (TEOS)), water glass and silica sol.

In some embodiments, the inorganic binder (e.g., silica) can be present in an amount ranging from about 0.1 wt.-% to about 40 wt.-%, in some embodiments from about 1.0 wt.-% to about 20 wt.-%, and in some embodiments from about 2.5 wt.-% to about 10 wt.-%, with respect to the solids content of the mixture, respectively.

In some embodiments, the inorganic binder can be present in an amount of at least about 0.1 wt.-%, in some embodiments at least about 1.0 wt.-%, and in some embodiments at least about 2.5 wt.-%, with respect to the solids content of the mixture, respectively.

In some embodiments, the inorganic binder can be present in an amount no greater than about 10 wt.-%, in some embodiments no greater than about 20 wt.-%, and in some embodiments no greater than about 40 wt.-%, with respect to the solids content of the mixture, respectively.

Glass and/or Glass Ceramic Powder

The nature and structure of the glass and/or glass ceramic powder to be used in a slurry is not particularly limited, either, unless the intended purpose cannot be achieved.

The glass and/or glass ceramic powder may consist essentially of, or consist only of a glass and/or glass ceramic material. The glass and/or glass ceramic material can be selected to be compatible for use in human bodies. Furthermore, the glass and/or glass ceramic material can be selected to provide good aesthetic appearance for the dental appliance.

In some embodiments, the glass and/or glass ceramic powder can be characterized by at least one of the following features:
 mean particle size: range from about 5 μm to about 60 μm, or from about 10 to about 40 μm (measured with laser diffraction);
 melting temperature: around or less than 1000° C. and/or
 density: about 2.0 to about 2.6 or about 2.2 to about 2.5 g/cm$^3$ (according to the technical data sheet provided by the manufacturer).

In some embodiments, a glass composition, which can be used, can include:
 silica: about 60 to about 70 wt.-%,
 alumina: about 9 to about 13 wt.-%,
 potassium-oxide: about 5 to about 10 wt.-%,
 sodium-oxide: about 9 to about 13 wt.-%,
 lithium-oxide: about 0 to abut 1 wt.-%,
 calcium oxide: about 2 to about 5 wt.-%,
 barium-oxide: about 0 to about 2 wt.-% (optional), zirconium oxide: about 0 to about 1 wt.-% (optional), and
cerium-oxide or cerium-fluoride: about 0 to about 1 wt.-% (optional).

Examples of glass and/or glass ceramic materials that can be used include those available under the designations: "VM 9" from Vita Zahnfabrik, Bad Säckingen, Germany, "Cerabien Zr" from Noritake Inc., Japan, "Vintage" from Shofu, Japan; "ZIROX" from Wieland GmbH & Co. KG, Pforzheim, Germany and LM-$ZrO_2$ from Chemichl, Liechtenstein.

In some embodiments, the glass and/or glass ceramic powder can be present in an amount of at least about 40 wt.-%, in some embodiments at least about 60 wt.-%, and in some embodiments at least about 65 wt.-%, with respect to the whole composition or mixture, respectively.

In some embodiments, the glass and/or glass ceramic powder can be present in an amount no greater than about 75 wt.-%, in some embodiments no greater than about 80 wt.-%, and in some embodiments no greater than about 85 wt.-%, with respect to the whole composition or mixture, respectively.

In some embodiments, the glass and/or glass ceramic powder can be present in an amount ranging from about 40 wt.-% to about 85 wt.-%, in some embodiments ranging from about 60 wt.-% to about 80 wt.-%, and in some embodiments ranging from about 65 wt.-% to about 75 wt.-%, with respect to the whole composition or mixture, respectively.

The distribution of the particle size may be for example:
10% of the particles smaller than about 5 µm or smaller than about 2 µm;
50% of the particles smaller than about 25 µm or smaller than about 10 µm; and
90% of the particles smaller than about 70 µm or smaller than about 40 µm.

Additives

A mixture or slurry of the present disclosure can also comprise further components or additives, such as colorant(s) and/or pigments (e.g. traces of fluorescent, organic pigments e.g. for easier identification of the blocks ("labeling"), which can be burnt out during firing; and/or inorganic pigments that remain in the appliance for coloration of the sintered material). Such additives or components can also be present or included in the glass and/or glass ceramic powder or particles. Suitable colorants can include one or more of the following elements or ions thereof: Fe, Mn, V, Cr, Zn, Sn and Co.

Further additives, which can be added, can include retarders, (such as 1,2-diphenylethylene), plasticizers (including polyethylene glycol derivatives, polypropylene glycols, low-molecular-weight polyesters, dibutyl, dioctyl, dinonyl and diphenyl phthalate, di(isononyl adipate), tricresyl phosphate, paraffin oils, glycerol triacetate, bisphenol A diacetate, ethoxylated bisphenol A diacetate, silicone oils, or a combination thereof), fluoride releasing materials, or a combination thereof.

Some embodiments include no additives, however, if they are present, they can be present in an amount of at least about 0.01 wt.-%, in some embodiments at least about 0.1 wt.-%, and in some embodiments at least about 1 wt.-%, with respect to the whole composition or mixture, respectively.

In some embodiments, additives can be present in an amount no greater than about 20 wt.-%, in some embodiments no greater than about 10 wt.-%, and in some embodiments no greater than about 5 wt.-%, with respect to the whole composition or mixture, respectively.

In some embodiments, additives can be included in amounts ranging from about 0.01 to about 20 wt.-%, in some embodiments ranging from about 0.1 to about 10 wt.-%, and in some embodiments ranging from about 1 to about 5 wt.-%.

As long as the additive does not influence the sol-gel reaction, it can be employed in any desired amount with respect to the whole composition or mixture.

In some embodiments, a slurry or mixture to be used in the casting process of the present disclosure can include the individual components in the following amounts:
liquid: from about 15 wt.-% to about 60 wt.-%, or from about 20 wt.-% to about 40 wt.-%, or from about 25 wt.-% to about 35 wt.-%, with respect to the whole weight of the mixture;
inorganic binder: from about 0.1 wt.-% to about 40 wt.-%, or from about 1 wt.-% to about 20 wt.-%, or from about 2.5 wt.-% to about 10 wt.-%, with respect to the solids content of the mixture;
glass and/or glass ceramic powder: from about 40 wt.-% to about 85 wt.-%, or from about 60 wt.-% to about 80 wt.-%, or from about 65 wt.-% to about 75 wt.-%, with respect to the whole weight of the mixture; and
additives (including colorant(s)): from about 0.01 to about 20 wt.-%, or from about 0.1 to about 10 wt.-%, or from about 1 to about 5 wt.-%, with respect to the whole weight of the mixture.

In some embodiments, the ratio (with respect to weight) of liquid to inorganic binder can be a range of about 10:1 to about 1:1, or from about 7:1 to about 3:1. If the ratio is outside this range, the obtained dental appliance may not include the desired properties.

In some embodiments, the ratio (with respect to weight) of inorganic binder to glass and/or glass ceramic powder can be in a range of about 1:100 to about 1:5, or from about 1:40 to about 1:10. If the ratio is outside this range, the obtained dental appliance may not include the desired properties.

Forming the Slurry

In some embodiments, the slurry or mixture can be obtained by the following exemplary process:
i) providing a liquid,
ii) adjusting the liquid to a pH value suitable to start the condensation reaction, depending on the binder precursor used (e.g. 10 to about 12 for TMOS or about 2 to about 4 for water glass),
iii) adding the glass and/or glass ceramic powder, and
iv) adding the inorganic binder,
wherein steps iii) and iv) can also be carried out in reverse order.

The pH value can be adjusted by using conventional basic reagents like NaOH, KOH or $NH_3$ containing solutions or acidic reagents like HCl or $HNO_3$ containing solutions, wherein the pH value can be determined during the adjustment step. The pH value can be determined by e.g. pH sensitive paper or electronic equipment (e.g. pH electrode). If strong acids or bases are employed, determination of the pH value can also be obtained via calculation from the amount of acid used.

The inorganic binder can be added rapidly while the solution is stirred. The addition of the inorganic binder can mark the starting point of a sol-gel reaction caused by the reaction of the inorganic binder molecules. In some embodiments, a two-slurry system can be used. If a two-slurry system ("I" and "II") is used, mixing of the two slurries marks the starting point of the sol-gel reaction.

During the sol-gel reaction, an inorganic network can be formed.

In some embodiments, providing a slurry or mixture can be characterized by at least one of the following features:
time needed for gelation (i.e. time from adding the inorganic binder until solidification of the mixture to the point that it cannot be deformed or removed from the mold by tilting the mold): 30 seconds to 5 minutes; and/or time needed for settling (i.e., time from stopping the mixture being stirred until the mixture becomes inhomogeneous because of settling of the glass and/or glass ceramic particles): 7 minutes to more than one week (values were obtained either without inorganic binder present or with binder present but at a pH value that inhibits gelation).

The mixtures or slurries to be used in the process of the present disclosure typically do not contain polymerizable organic binder components like (meth)acrylate or epoxy groups containing components.

That is, in some embodiments, the mixture is essentially free of polymerizable organic binder components. An organic binder within the meaning of the invention is a binder, which consists of organic compounds that are added to strengthen the appliance or workpiece and cannot be thermally removed from the workpiece below a temperature of 200° C. Organic binders can produce gases like carbon oxide(s) or nitrogen oxide(s) when heated above the combustion temperature. These exhaust gases may have to be removed by expensive air treatment or chimneys.

In some embodiments, the addition or presence of an initiator (e.g. photo or redox initiator) for starting the hardening process of the inorganic binder is typically not needed. The hardening process can be initiated by adjusting the pH value or simply by employing a diluted acidic/basic solution.

The production process of the present disclosure typically also does not include a pressing step (e.g. isostatic or uniaxial) or a pre-sintering step.

The following embodiments are intended to be illustrative of the present disclosure and not limiting.

EMBODIMENTS

Embodiment 1 is a method for making a layered dental appliance, the method comprising: providing a dental core; providing a first mold comprising a negative of a first layer of a layered dental appliance; positioning a first slurry in the first mold; pressing the dental core into the first slurry in the first mold to form a first article comprising the dental core and a first layer formed from the first slurry; removing the first article from the first mold; providing a second mold comprising a negative of a second layer of a layered dental appliance; positioning a second slurry in the second mold; and pressing the first article into the second slurry in the second mold to form a second article comprising the dental core, the first layer, and a second layer formed from the second slurry.

Embodiment 2 is the method of embodiment 1, further comprising firing the first article prior to pressing the first article into the second slurry in the second mold, wherein firing the first article causes at least a portion of the first article to shrink.

Embodiment 3 is the method of embodiment 1 or 2, further comprising firing the second article.

Embodiment 4 is the method of any of embodiments 1-3, further comprising: removing the second article from the second mold; and firing the second article.

Embodiment 5 is the method of any of embodiments 2-4, wherein firing the first article includes firing the first article at a temperature of at least 500° C.

Embodiment 6 is the method of embodiment 1 or 2, further comprising: removing the second article from the second mold; providing a third mold comprising a negative of a third layer of a dental appliance; positioning a third slurry in the third mold; and pressing the second article into the third slurry in the third mold to form a third article comprising the dental core, the first layer, the second layer, and a third layer formed from the third slurry.

Embodiment 7 is the method of embodiment 6, wherein the third layer forms the outermost layer of the layered dental appliance.

Embodiment 8 is the method of embodiment 6 or 7, wherein the third slurry is formed of the same material as at least one of the first slurry and the second slurry.

Embodiment 9 is the method of any preceding embodiment, further comprising activating at least one of the first slurry and the second slurry prior to positioning the first slurry and the second slurry in the first mold and the second mold, respectively.

Embodiment 10 is the method of any preceding embodiment, further comprising initiating a sol-gel reaction in at least one of the first slurry and the second slurry prior to positioning the first slurry and the second slurry in the first mold and the second mold, respectively.

Embodiment 11 is the method of any preceding embodiment, further comprising drying at least one of the first article and the second article.

Embodiment 12 is the method of any preceding embodiment, further comprising machining at least one of the first layer and the second layer.

Embodiment 13 is the method of any preceding embodiment, wherein providing the mold includes preparing a mold based on a digital workflow.

Embodiment 14 is a system for making a layered dental appliance, the system comprising: a first mold comprising a negative of a first layer of a layered dental appliance; a second mold comprising a negative of a second layer of a layered dental appliance; a dental core dimensioned to be at least partially received in the first mold and the second mold; a first slurry adapted to be positioned in the first mold to form a first article comprising a first layer on the dental core, wherein the second mold is dimensioned to receive the first article; and a second slurry adapted to be positioned in the second mold to form a second layer on the first article.

Embodiment 15 is the system of embodiment 14, further comprising: a third mold comprising a negative of a third layer of a layered dental appliance; and a third slurry adapted to be positioned in the third mold to form a third layer on the dental core.

Embodiment 16 is the method of any of embodiments 1-13 or the system of claim 14 or 15, wherein the second mold is different from the first mold.

Embodiment 17 is the method of any of embodiments 1-13 and 16 or the system of any of embodiments 14-16, wherein the first mold comprises a first negative of a first layer and the second mold comprises a second negative of a second layer, and wherein the first negative and the second negative are different.

Embodiment 18 is the method of any of embodiments 1-13 and 16-17 or the system of any of embodiments 14-17, wherein the first mold comprises an enlarged negative of a first layer of a layered dental appliance.

Embodiment 19 is the method of any of embodiments 1-13 and 16-18 or the system of any of embodiments 14-18, wherein the second mold comprises an enlarged negative of a second layer of a layered dental appliance.

Embodiment 20 is the method of any of embodiments 1-13 and 16-19 or the system of any of embodiments 14-19, wherein the first layer is positioned intermediately of the dental core and the second layer.

Embodiment 21 is the method of any of embodiments 1-13 and 16-20 or the system of any of embodiments 14-20, wherein the dental core includes at least one of a ceramic, a metal, a metal alloy, a precious metal, a precious metal alloy, and a combination thereof.

Embodiment 22 is the method of any of embodiments 1-5, 9-13 and 16-21 or the system of any of embodiments 14 and 16-21, wherein the second layer forms the outermost layer of the layered dental appliance.

Embodiment 23 is the method of any of embodiments 1-13 and 16-22 or the system of any of embodiments 14-22, wherein at least a portion of at least one of the first mold and the second mold is formed of at least one of silicone, polyethylene (PE), polypropylene (PP), polycarbonate, polyurethane, polystyrene, polyoxymethylene, a metal, and a combination thereof.

Embodiment 24 is the method of any of embodiments 1-13 and 16-23 or the system of any of embodiments 14-23, wherein at least one of the first slurry and the second slurry comprises at least one of a glass powder, a glass ceramic powder, and a combination thereof.

Embodiment 25 is the method of any of embodiments 1-13 and 16-24 or the system of any of embodiments 14-24, wherein at least one of the first slurry and the second slurry comprises at least one of a glass slurry, a glass ceramic slurry, and a combination thereof.

Embodiment 26 is the method of any of embodiments 1-13 and 16-25 or the system of any of embodiments 14-25, wherein at least one of the first slurry and the second slurry comprises: (i) at least one of a glass powder and a glass ceramic powder; (ii) a liquid; and (iii) an inorganic binder.

Embodiment 27 is the method of any of embodiments 1-13 and 16-26 or the system of any of embodiments 14-26, wherein the second slurry is formed of a different material than the first slurry.

Embodiment 28 is the method of any of embodiments 1-13 and 16-27 or the system of any of embodiments 14-27, wherein the dental core comprises a completely sintered ceramic.

The following working example is intended to be illustrative of the present disclosure and not limiting.

EXAMPLES

Example 1

Formation of a Two-Layer Appliance

A plaster and silicone mold was formed in the following way: A model of an incisor formed of polyoxymethylene (available under the trade designation DELRIN from DuPont Corp., Wilmington, Del.) was partially embedded into a small cube of molten wax (supported in a small box to contain the liquid wax), occlusal half in the wax and the root half facing up, free of wax. The wax was allowed to harden by cooling it at ambient conditions. The solid wax cube having the incisor was then embedded in a block of dental plaster (supported in a small box to contain the wet plaster) such that the top surface of the wax cube was level with the top surface of the plaster, leaving the root of the incisor exposed. The plaster block was dried and four registration features were carved into the top surface of the plaster, forming radial depressions that later mated with corresponding protrusions on a top plaster mold. A spray release agent was applied to the top of the plaster and wax, taking care to keep the exposed root free of release agent.

To form the top half of the mold, wet plaster was poured on top of the finished bottom mold (supported in a small box to contain the wet plaster) having the incisor root exposed. After drying, the top half of the mold exactly mated to the bottom half because of the registration features, and the root was now attached to the top half of the mold and exactly registered with the wax cube. The top and bottom halves were separated and the wax was removed from the bottom half and cleaned from the occlusal half of the incisor.

The now-empty cavity in the bottom half was filled with polydimethyl methylphenyl siloxane (Heraform, type A+B, Heraeus Kulzer, Germany) and the top half was put in place while the silicone cured. This formed a silicone mold having a cavity that included a negative of the shape of the model incisor, which was the outer shape of the desired layered dental appliance (i.e., a dental restoration). The halves were again separated and the incisor was ground to a smaller size to function as a "stump" support for a zirconia dental core, which had been formed using a LAVA™ digital system (available from 3M ESPE AG, Seefeld, Germany). The stump was made to fit the interior of the zirconia core using a drop of wax, which adhered to the stump, but not to the zirconia core.

A first slurry was prepared by mixing 0.2 ml silica sol (Levasil 200/40%, Obermeier, Germany), 0.7 ml of deionized water, and 3.0 g of glass powder (Dentin A4, brown, from Chemichl, Lichtenstein). To the mixture, 0.02 ml of 30% hydrochloric acid (Fluka, Germany) was added, thus initiating the hardening reaction. Thirty seconds later, the slurry was poured into the bottom, negative portion of the mold and the zirconia dental core was pressed into the slurry by placing the top half of the mold into position with respect to the bottom half of the mold. After hardening for 70 min. at room temperature, the mold was placed into a drying oven (Memmert, Germany) at 50° C. for 120 min. After removal from the oven and cooling, the two halves of the mold were separated, leaving a solidified layer of glass on the zirconia core, having the exterior shape of the crown (i.e., the incisor that was used to form the mold). The wax attachment allowed easy separation of the zirconia core and attached layer of glass from the stump. Core and glass layer were fired under vacuum at 790° C. in an Austromat 3001 furnace (Dekema, Germany) for 25 min. After firing, the glass layer, simulating dentin, had shrunk to a smaller size, being smaller than the original mold cavity. The first article comprising the zirconia dental core the first glass layer was reattached to the waxed stump in the top half of the mold.

A second slurry was prepared in the same manner as the first slurry, except that the glass powder used was Incisal 2 (Chemichl), which simulated the translucent enamel layer of natural teeth. As described above, the second slurry was placed into the same bottom mold cavity and the first article was pressed into the second slurry by placing the top half of the mold into position with respect to the bottom half of the mold. After drying the second slurry following the same process that was used to dry the first slurry, a second article comprising the zirconia dental core and two layers of coating was removed from the mold and fired, this time at 780° C. for 25 min.

The resulting layered appliance was a crown restoration and had a zirconia dental core, a first layer simulating dentin and a second outermost layer having a translucency that simulated natural enamel.

The embodiments described above and illustrated in the figure are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure. Various features and aspects of the present disclosure are set forth in the following claims.

What is claimed is:

1. A method for making a layered dental appliance, the method comprising:
   providing a dental core comprising at least one of completely sintered ceramic, a metal, a metal alloy, a precious metal, a precious metal alloy, or a combination thereof, wherein the dental core forms a portion of the layered dental appliance;
   providing a first mold comprising a negative of a first layer of a layered dental appliance;
   positioning a first slurry in the first mold;
   pressing the dental core into the first slurry in the first mold to form a first article comprising the dental core and a first layer formed from the first slurry;
   removing the first article from the first mold;
   providing a second mold comprising a negative of a second layer of a layered dental appliance, wherein the second mold is different from the first mold;
   positioning a second slurry in the second mold; and
   pressing the first article into the second slurry in the second mold to form a second article comprising the dental core, the first layer, and a second layer formed from the second slurry.

2. The method of claim 1, further comprising firing the first article after removing the first article from the first mold and prior to pressing the first article into the second slurry in the second mold, wherein firing the first article causes at least a portion of the first article to shrink.

3. The method of claim 1, further comprising firing the second article.

4. The method of claim 1, further comprising:
   removing the second article from the second mold; and
   firing the second article after removing the second article from the second mold.

5. The method of claim 2, wherein firing the first article includes firing the first article at a temperature of at least 500° C.

6. The method of claim 1, further comprising:
   removing the second article from the second mold;
   providing a third mold comprising a negative of a third layer of a dental appliance;
   positioning a third slurry in the third mold; and
   pressing the second article into the third slurry in the third mold to form a third article comprising the dental core, the first layer, the second layer, and a third layer formed from the third slurry.

7. The method of claim 1, further comprising activating at least one of the first slurry and the second slurry prior to positioning the first slurry and the second slurry in the first mold and the second mold, respectively.

8. The method of claim 1, further comprising initiating a sol-gel reaction in at least one of the first slurry and the second slurry prior to positioning the first slurry and the second slurry in the first mold and the second mold, respectively.

9. The method of claim 1, wherein the first mold comprises a first negative of a first layer and the second mold comprises a second negative of a second layer, and wherein the first negative and the second negative are different.

10. The method of claim 1, wherein at least a portion of at least one of the first mold and the second mold is formed of at least one of silicone, polyethylene (PE), polypropylene (PP), polycarbonate, polyurethane, polystyrene, polyoxymethylene, a metal, and a combination thereof.

11. The method of claim 1, wherein at least one of the first slurry and the second slurry comprises:
   (i) at least one of a glass powder and a glass ceramic powder;
   (ii) a liquid; and
   (iii) an inorganic binder.

* * * * *

UNITED STATES PATENT AND TRADEMARK OFFICE
CERTIFICATE OF CORRECTION

PATENT NO.        : 8,834,752 B2
APPLICATION NO.   : 13/497410
DATED             : September 16, 2014
INVENTOR(S)       : Martin Goetzinger et al.

It is certified that error appears in the above-identified patent and that said Letters Patent is hereby corrected as shown below:

In the Specification

Column 20
Line 65, Delete "abut" and insert -- about --, therefor.

Column 26
Line 26, Delete "Lichtenstein)." and insert -- Liechtenstein). --, therefor.

Signed and Sealed this
Tenth Day of February, 2015

Michelle K. Lee
*Deputy Director of the United States Patent and Trademark Office*